(12) United States Patent
Reyes

(10) Patent No.: US 7,850,670 B2
(45) Date of Patent: Dec. 14, 2010

(54) BETTER FIT TO THE BOTTOM AREA OF A DISPOSABLE PRODUCT

(75) Inventor: Loida Guzman Reyes, Philadelphia, PA (US)

(73) Assignee: First Quality Retail Services, LLC, Great Neck, NY (US)

( * ) Notice: Subject to any disclaimer, the term of this patent is extended or adjusted under 35 U.S.C. 154(b) by 0 days.

(21) Appl. No.: 11/528,068

(22) Filed: Sep. 27, 2006

(65) Prior Publication Data

US 2008/0077115 A1  Mar. 27, 2008

(51) Int. Cl.
*A61F 13/15* (2006.01)
*A61F 13/20* (2006.01)

(52) U.S. Cl. .................. 604/385.03; 604/387; 604/392

(58) Field of Classification Search ............ 604/385.01, 604/385.03, 387–392
See application file for complete search history.

(56) References Cited

U.S. PATENT DOCUMENTS

| | | | |
|---|---|---|---|
| 2,256,510 A * | 9/1941 | Young | 604/386 |
| 4,850,988 A | 7/1989 | Aledo et al. | |
| 4,938,753 A | 7/1990 | Van Gompel et al. | |
| 4,940,464 A | 7/1990 | Van Gompel et al. | |
| 5,151,092 A | 9/1992 | Buell et al. | |
| 5,176,670 A | 1/1993 | Roessler et al. | |
| 5,496,298 A | 3/1996 | Kuepper et al. | |
| 5,503,919 A | 4/1996 | Litchholt et al. | |
| 5,514,470 A | 5/1996 | Haffner et al. | |
| 5,527,304 A | 6/1996 | Buell et al. | |
| 5,591,155 A | 1/1997 | Nishikawa et al. | |
| 5,601,547 A | 2/1997 | Kato et al. | |
| 5,674,216 A | 10/1997 | Buell et al. | |
| 5,685,873 A | 11/1997 | Bruemmer | |
| 5,807,368 A | 9/1998 | Helmer | |
| 5,897,545 A | 4/1999 | Kline et al. | |
| 5,931,825 A | 8/1999 | Kuen et al. | |
| 5,957,908 A | 9/1999 | Kline et al. | |
| 6,287,287 B1 | 9/2001 | Elsberg | |
| 6,306,121 B1 * | 10/2001 | Damaghi et al. | 604/385.03 |
| 6,352,528 B1 | 3/2002 | Weber et al. | |
| 6,406,467 B1 | 6/2002 | Dilnik et al. | |
| 6,406,468 B1 | 6/2002 | Dilnik et al. | |
| 6,428,526 B1 | 8/2002 | Heindel et al. | |
| 6,447,497 B1 | 9/2002 | Olson | |
| 6,454,751 B1 | 9/2002 | Olson | |
| 6,459,014 B1 | 10/2002 | Chmielewski et al. | |
| 6,476,289 B1 | 11/2002 | Buell et al. | |
| 6,491,677 B1 | 12/2002 | Glaug et al. | |

(Continued)

OTHER PUBLICATIONS

U.S. Appl. No. 11/238,738, Edward Erman, Entire Document.

*Primary Examiner*—Michele Kidwell
(74) *Attorney, Agent, or Firm*—Amster, Rothstein & Ebenstein LLP

(57) ABSTRACT

An absorbent article is provided with a chassis having an anterior portion and a crotch portion and a belt coupled to the chassis. The belt has end portions extending outwardly beyond side edges of the chassis. The end portions of the belt are configured to be fastened between the crotch portion and the anterior portion, and the belt is configured to draw the crotch portion toward the anterior portion of the chassis about a body portion of a wearer to limit sag and leakage at the crotch portion of the chassis.

12 Claims, 7 Drawing Sheets

U.S. PATENT DOCUMENTS

| | | |
|---|---|---|
| 6,500,162 B1 | 12/2002 | Freiburger et al. |
| 6,503,239 B1 | 1/2003 | Bruemmer-Prestley et al. |
| 6,508,799 B1 | 1/2003 | Freiburger et al. |
| 6,511,465 B1 | 1/2003 | Freiburger et al. |
| 6,514,235 B1 | 2/2003 | Freiburger et al. |
| 6,520,946 B1 | 2/2003 | Krueger |
| 6,524,293 B1 | 2/2003 | Elsberg et al. |
| 6,544,244 B1 | 4/2003 | Glaug et al. |
| 6,548,732 B2 | 4/2003 | Erdman et al. |
| 6,551,430 B1 | 4/2003 | Glaug et al. |
| 6,554,816 B1 | 4/2003 | Olson |
| 6,566,578 B1 | 5/2003 | Glaug et al. |
| 6,569,141 B1 | 5/2003 | Bruemmer-Prestley et al. |
| 6,572,595 B1 | 6/2003 | Klemp et al. |
| 6,575,949 B1 | 6/2003 | Waksmundzki et al. |
| 6,575,950 B1 | 6/2003 | Waksmundzki et al. |
| 6,575,953 B2 | 6/2003 | Olson |
| 6,605,173 B2 | 8/2003 | Glaug et al. |
| 6,607,515 B2 | 8/2003 | Glaug et al. |
| 6,627,289 B1 | 9/2003 | Dilnik et al. |
| 6,645,190 B1 | 11/2003 | Olson et al. |
| 6,667,085 B1 | 12/2003 | McNichols |
| 6,692,477 B2 | 2/2004 | Gibbs |
| 6,740,071 B2 | 5/2004 | Gibbs |
| 2006/0247598 A1 * | 11/2006 | Roehrl et al. ............... 604/392 |

* cited by examiner

BETTER FIT TO THE BOTTOM AREA OF A DISPOSABLE PRODUCT

FIELD OF THE INVENTION

The present invention relates to an absorbent article having a belt for drawing the absorbent article toward the body of a wearer.

BACKGROUND OF THE INVENTION

Disposable absorbent articles, such as disposable diapers and disposable pant-type garments (sometimes referred to as training pants) have found widespread acceptance for infant care. Garments of this nature are typically configured for a single use, with an absorbent panel or core of the construction ordinarily provided in an integrated structure including a liquid-pervious top sheet or body facing layer, and a back sheet or garment facing layer having at least a portion which is liquid impervious. Adhesive coated fastening tabs or hook-and-loop fasteners are typically provided on disposable diapers, while pant-type garments typically include side seams which can be readily torn for removal of the garment if soiled. Absorbent articles of the above nature are not only suitable for infants, but can be appropriately sized and configured for incontinence use by adults.

Conventional disposable absorbent garments commonly exhibit performance issues such as sag and leakage at the crotch portion. There is therefore a continued need for improved absorbent garments.

SUMMARY OF THE INVENTION

According to one aspect of this invention, an absorbent article is provided with a chassis having a waist edge extending between side edges. The absorbent article is also provided with a belt coupled to the chassis, the belt having a central portion extending between the side edges of the chassis and end portions extending outwardly beyond the side edges of the chassis. A distance between the central portion of the belt and the waist edge of the chassis is greater than a distance between the end portions of the belt and the waist edge of the chassis at the side edges of the chassis.

According to another aspect of this invention, an absorbent article is provided with a chassis having an anterior portion and a crotch portion, and a belt coupled to the chassis. The belt has end portions extending outwardly beyond side edges of the chassis. The end portions of the belt are configured to be fastened between the crotch portion and the anterior portion, and the belt is configured to draw the crotch portion toward the anterior portion of the chassis about a body portion of a wearer to limit sag and leakage at the crotch portion of the chassis.

According to yet another aspect of this invention, a method is provided for forming an absorbent article. The method includes coupling a central portion of a belt to a chassis such that end portions of the belt extend beyond side edges of the chassis. The belt is also oriented such that a distance between the central portion of the belt and a waist edge of the chassis is greater than a distance between the end portions of the belt and the waist edge of the chassis at the side edges of the chassis.

BRIEF DESCRIPTION OF THE DRAWINGS

The invention is best understood from the following detailed description when read in connection with the accompanying drawings. It is emphasized that, according to common practice, the various features of the drawings may not be to scale. On the contrary, the dimensions of the various features may be arbitrarily expanded or reduced for clarity. Included in the drawing are the following figures.

DETAILED DESCRIPTION OF THE INVENTION

Figure 1A:
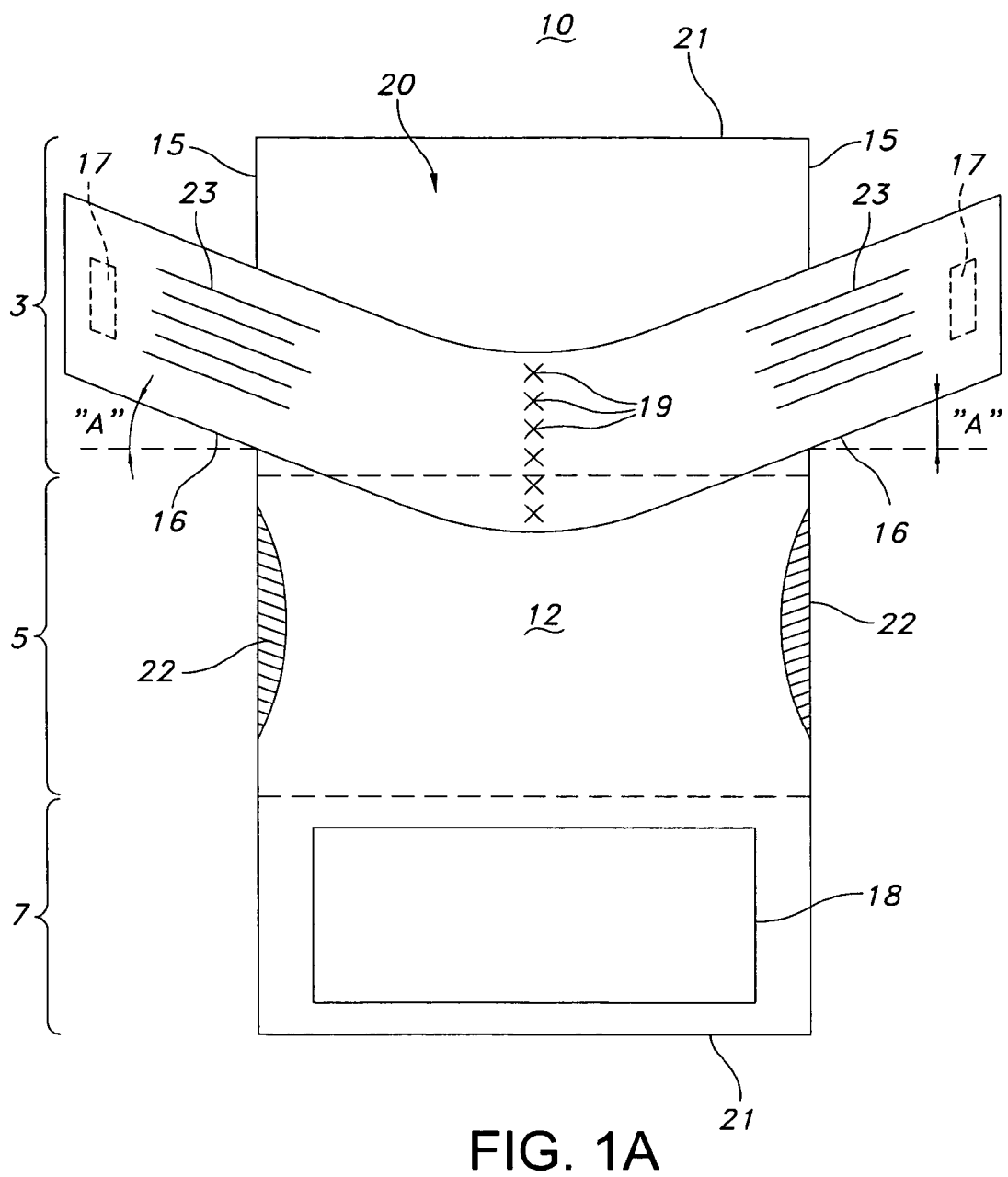
FIG. 1A is a plan view of the garment facing side of an exemplary absorbent article.

The invention will next be illustrated with reference to the figures. Such figures are intended to be illustrative rather than limiting and are included herewith to facilitate explanation of the present invention. The figures are not to scale, and are not intended to serve as engineering drawings.

Generally, a disposable absorbent article embodying the principles of the present invention can be configured as a disposable diaper, or a pant-type garment, for infants or small children, or can be appropriately sized and configured for use by incontinent adults. For enhancing the containment and fit characteristics of the article, the absorbent article according to one embodiment includes one or more elasticized belts or stretch ears that are extendable from the mid-section and rear of the article and configured to be fastened to the front of the article to draw portions of the article against the body of the wearer.

With reference now to the drawings, therein is illustrated exemplary embodiments of disposable absorbent articles 10, 110, 210 and 310, such as diapers or adult-incontinence products. As used in the present disclosure, the term "absorbent article" is intended to refer to an article or garment which is worn by an individual for absorbing urine, fecal matter or other body fluids. It is understood that garments embodying the principles of the present invention can be appropriately sized for use by infants and children, and can further be sized for use by incontinent adults.

Each absorbent article 10, 110, 210 and 310 comprises a chassis 20, 120, 220 and 320 including a liquid pervious top sheet 14, 114, 214 and 314 being positionable generally adjacent to the body of a wearer during use of the article. The article further includes a backsheet 12, 112, 212 and 312 preferably having at least a portion which is liquid impervious, with the backsheet being positionable generally adjacent to a garment, e.g., pants, of a wearer during use of the article. An absorbent core 25 is positioned between the top sheet and the back sheet for absorbing body fluid.

Referring generally to the exemplary embodiments illustrated in the figures, each absorbent article chassis 20, 120, 220 and 320 is generally composed of three adjoining portions, namely, a posterior portion 3, a crotch portion 5, and an anterior portion 7. The boundaries of the respective portions of the chassis 20, 120, 220 and 320 are demarcated by the broken lines shown in FIGS. 1A and 1B. It should be understood that the boundaries of the respective chassis portions are approximate, and may vary accordingly.

The crotch portion 5 of the chassis generally corresponds to that portion which is positioned between the legs of a wearer adjacent the genitalia, and as used herein, comprises about one-third of the longitudinally central portion of the chassis. The crotch portion 5 includes the "target" or fluid "insult" zone, i.e., the area at which the body fluid(s) gain(s) ingress into the article. The posterior portion 3 of the chassis is generally positioned adjacent the buttocks and rear waist of the wearer, and comprises about one-third of the longitudinal portion of the chassis 20, 120, 220 and 320. The anterior portion 7 of the chassis is generally positioned adjacent the frontal region of a wearer, and comprises about one-third of the longitudinal portion of the chassis. As mentioned previously, the boundaries of the respective chassis portions are approximate, and may vary accordingly.

In use, the exposed waist edges 21, 121, 221 and 321 of the posterior and anterior portions 3 and 7 of the chassis form the waist segment of the article. Although not shown, the exposed waist edges of the posterior and anterior portions 3 and 7 may be joined together about the waist of the wearer by a fastener, such as adhesive tape segments, or an integral adhesive tab.

The exemplary absorbent articles are particularly adapted to support the crotch portion 5 of the absorbent article. The article includes an elasticized belt 16, 116, 316 or a stretch ear 216 that is configured to draw the crotch and waist portions of the chassis against the body of the wearer. The elasticized belts and stretch ears are configured to conform to diverse waist, leg, and absorbent article chassis sizes, by virtue of the elasticity of the belts and ears.

Other features and advantages of the present invention will be readily apparent from the following detailed description of the embodiments thereof, taken in conjunction with the accompanying drawings described below wherein like elements have like numerals throughout the drawing figures.

Figure 1B:
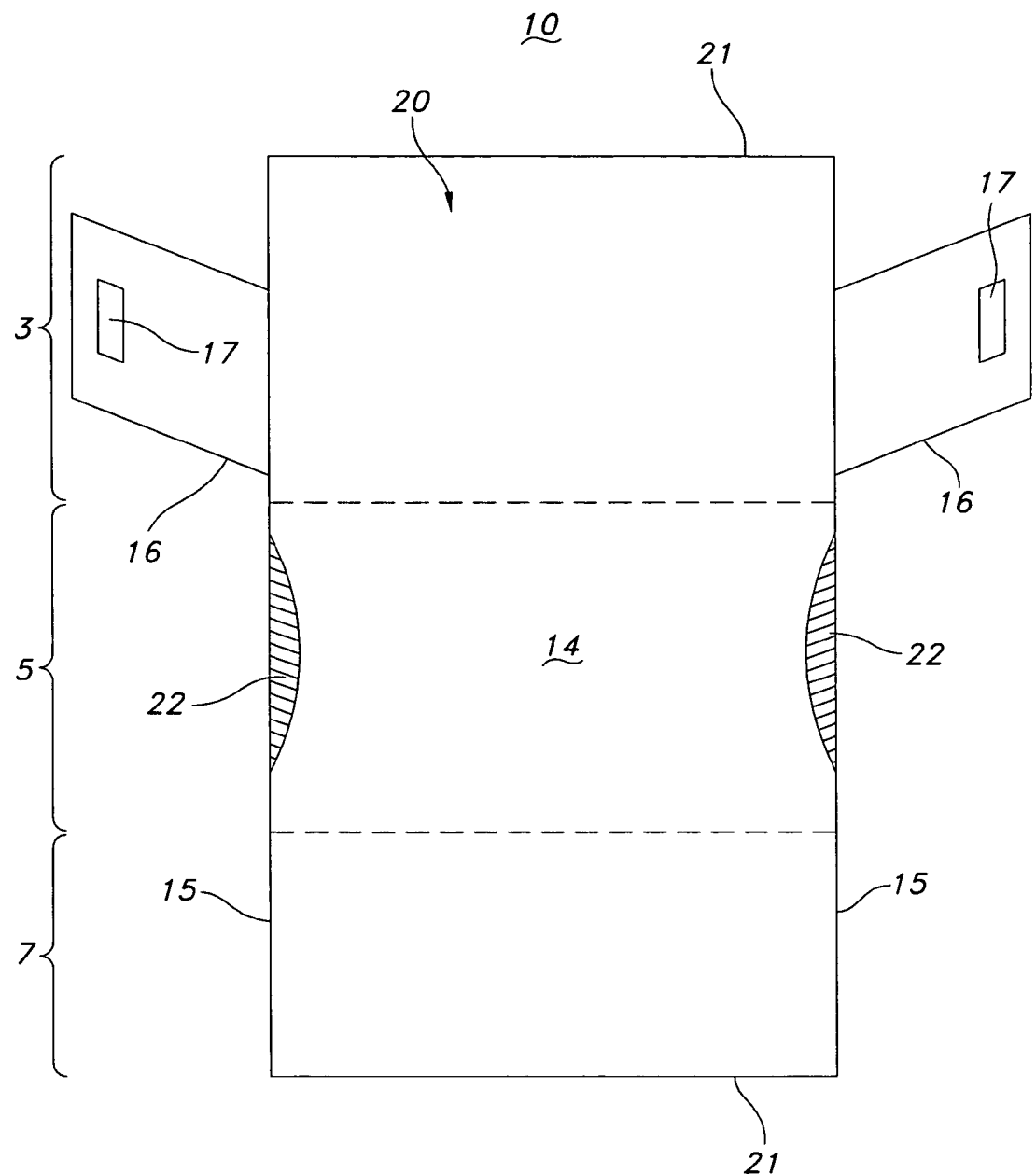
FIG. 1B is a plan view of the body facing side of the absorbent article of FIG. 1A.
Figure 1C:
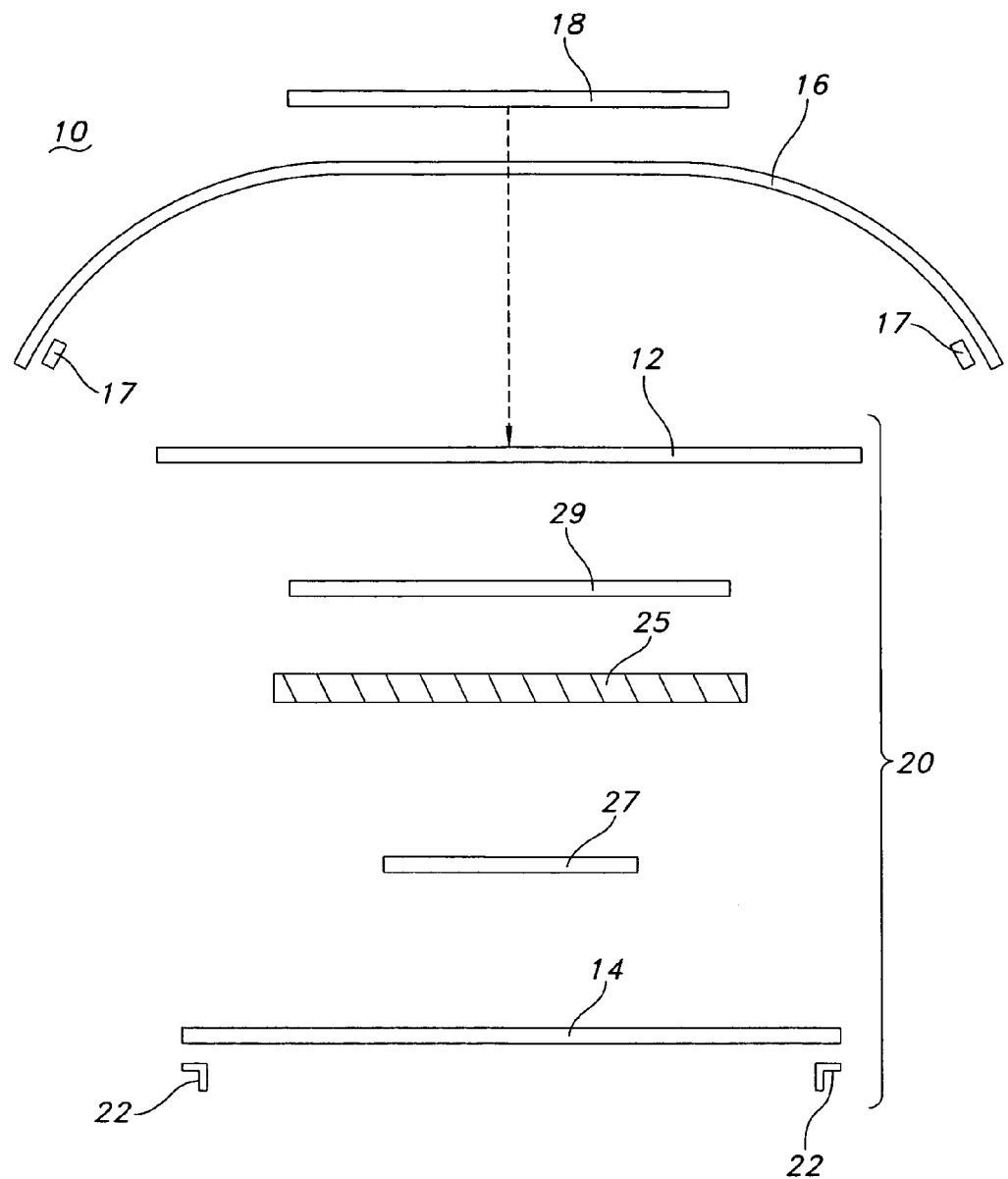
FIG. 1C is an exploded end view of the absorbent article of FIG. 1A.

Referring now to the exemplary embodiment illustrated in FIGS. 1A-1C, an absorbent article, such as a diaper or adult-incontinence product, is denoted by the numeral "10." The absorbent article 10 comprises a chassis 20 including a liquid pervious body-side liner or top sheet 14, with the top sheet 14 being positionable generally adjacent to the body of a wearer during use of the article. The chassis 20 further includes an outer cover or backsheet 12 preferably having at least a portion which is liquid impervious, with the backsheet 12 being positionable generally adjacent to a garment, e.g., pants, of a wearer during use of the article. An absorbent core 25 is positioned between the top sheet and the back sheet for absorbing body fluid.

The exemplary absorbent article 10 includes an elasticized belt 16 positioned on the backsheet 12 of the chassis 20. The central portion of the belt 16 (or any other suitable portion) is fastened or coupled or merely positioned adjacent to the posterior and crotch portions 3 and 5 of the chassis 20 at multiple sites such as attachment sites 19. The central portion of the belt refers to the portion of the belt 16 extending between the longitudinal edges 15 of the article. The longitudinal edges 15 are also referred to herein as side edges. The end portions of the belt 16, i.e., the unconstrained segments of the belt, extend beyond the opposing longitudinal edges 15 of the chassis 20.

In practice as a user dons the absorbent article, the user extends the end portions of the belt 16 toward the waist edge 21 of the anterior portion 7, thereby drawing the crotch portion 5 in the upward direction against the inner thigh of the wearer. To facilitate upward extension of the belt ends, the end portions of belt 16 extend beyond the longitudinal edges 15 along an angle "A", as best shown in FIG. 1A. Additionally, the distance between the central portion of the belt and the posterior waist edge 21 of the chassis is greater than the distance between the end portions of the belt and the posterior waist edge 21 of the chassis. In this manner, in use, the end portions of the belt extend upward toward the anterior portion 7, thereby drawing the crotch portion of the chassis toward the anterior portion of the chassis about a leg, thigh, or buttocks of a wearer.

The central portion of the belt 16 is optionally coupled to the chassis. For example, it is optionally bonded to the back sheet 12 at one attachment site or multiple attachment sites 19 by any bonding means known in the art, such as heat sealing, ultrasonic bonding, stitching or the like. At least one or more of the attachment sites 19 are preferably located on the crotch portion 5 of the chassis 20 to draw the crotch portion 5 against the crotch region of the wearer, while the attachment sites 19 are also preferably located on the posterior portion 3 of the chassis 20 to draw the posterior portion 3 of the chassis 20 against the buttocks, hips and waist of the wearer. The size and number of attachment sites 19 (six shown for purposes of illustration in FIG. 1A) influence the elasticity and elongation length of the belt 16, and may vary accordingly. The elasticity of the belt 16 diminishes for an increasing number and/or size of attachment sites 19. The belt 16 is not limited to the illustration shown, as the belt 16 may include any number, size, or pattern of attachment sites 19 or may be provided without attachment sites. Accordingly, it follows that the length, width and shape of the belt 16 may vary to accommodate any desired number, size, or pattern of attachment sites 19.

In this exemplary embodiment, the elasticized belt 16 is optionally formed from an elasticized material comprising elastic elements 23 that extend along the length of the belt 16, as best shown schematically in FIG. 1A. The length, elasticity and elongated length of the belt 16 may vary to conform to users of varying waist and leg sizes as well as the size of the chassis 20. The elasticity of the belt 16 is primarily influenced by the elasticity of the belt fabric, as well as the elasticity, number, and size of the elastic elements 23 within the belt 16.

The end portions of the elasticized belt are configured to be releasably coupled to the anterior portion 7 of the chassis. At least one fastener 17 is provided at each end portion of the elasticized belt 16. The fasteners 17 may comprise any particular shape or size, or, alternatively, may be integral with the material of belt 16. For example, although not shown, the entire belt 16 may be formed from hook or loop material, thereby eliminating the need for an additional fastener component, such as fastener 17.

In this exemplary embodiment, the fasteners 17 are configured to be releasably coupled to a complimentary fastener 18, such as a landing zone, positioned on the anterior portion 7 of the back sheet 12. In use, the end portions of the belt 16 are extended toward the anterior portion 7 of the chassis 20, and the fasteners 17 are coupled to the fastener 18. The fastener 18 may represent a single component, as shown, or multiple components positioned along the back sheet 12 of the anterior portion 7. The surface area of fastener 18 may be large enough to cover at least a portion of the anterior portion 7, such that a user can position the fasteners 17 in a wide range of locations on fastener 18 to compensate for varying waist, leg and chassis sizes.

The fasteners 17 and 18 may be composed of hook or loop material such as VELCRO material available from Velcro USA Inc. of Manchester, N.H. USA. Alternatively, the fasteners 17 may embody a position adhesive with a release liner (release liner not shown). In use, after removal of the release liner from the position adhesive, the position adhesive may be coupled to a surface of the anterior portion 7 of the back sheet 12. The position adhesive fasteners 17 may also be coupled to a surface of an opposing belt 16, which may be particularly beneficial for users having a narrow waist or oversized chassis 20 (relative to the waist size of the wearer). Thus, the surfaces of the back sheet 14 and the belts 16 may be capable of being adhered to. In such an embodiment, the fastener 18 may be omitted from the article 10. If the adhesive bond between fastener 17 and the back sheet 12 is relatively permanent, the belt 16 may be formed from a material that can be readily torn for removal of the article if soiled, or, the belt may include a perforated portion (not shown) that can be readily separated.

Referring specifically to schematic FIG. 1C, the chassis 20 of the absorbent article 10 generally comprises the top sheet 14, a liquid transfer layer 27, an absorbent structure or core 25, a film layer 29, the back sheet 12, and a pair of opposed dual gather leg cuff assemblies 22. The liquid transfer layer 27, film layer 29 and cuff assemblies 22 are optional components of the chassis 20.

The top sheet 14 is positioned to face the body of the wearer, with the back sheet 12 facing away from the wearer. The top sheet 14 is superimposed over the back sheet 12, with the liquid transfer layer 27, absorbent core 25, and film layer 29 interposed therebetween. The top sheet 14 may be coextensive in size and shape with the back sheet 12, as shown, or alternatively, may only cover a portion of the back sheet 12. The back sheet 12 in combination with the top sheet 14, defines the extents of the article 10. The top sheet 14 is bonded to the back sheet 12 around its periphery. The back sheet 12 and top sheet 14 can be joined together in any suitable manner, e.g., by adhesive bonding. The adhesives can be applied in any manner such as by spraying, slot-coat extrusion, printing, or the like. The applied adhesive can be in any desired configuration or design, such as continuous or discontinuous beads, continuous or discontinuous swirls, meltblown patterns, spray patterns, or the like. Alternatively, the joining of layers and structures can be accomplished by heat sealing, ultrasonic bonding, or the like.

The belt 16 is mounted to the back sheet 12 of the chassis 12 by any bonding means known in the art, such as heat sealing, ultrasonic bonding, stitching or the like. The fastener 18 is also coupled to the back sheet 12, as indicated by the dotted line extending between the fastener 18 and the back sheet 12.

The back sheet 12 or cover is preferably formed of a laminated sheet of a non-woven material. The material of the back sheet 12 should be hydrophobic, soft in texture, and strong in tensile strength. One particularly suitable material is a spunbond-meltblow-spunbond (SMS) web, available from AVGOL Nonwoven Industries LTD., Holon, Israel. The spunbond layer is preferably made of polypropylene fibers. Such composites provide the dual advantages of liquid barrier properties of film along with a soft, warm outer fabric texture. The non-woven outer cover can also be made of other suitable cloth-like materials, e.g., spun-bond or thermal-bond nonwoven web made of either polypropylene, polyethylene, polyester, bi-component fibers (polyethylene/polypropylene or polyethylene/polyester), or any combinations of these fibers. Various multiple layer configurations or fiber denier variations may be used. Another example includes hydroentangled non-woven webs, which may contain some cotton and/or rayon fibers blending in with thermal-plastic fibers. Cellulose fibers can also be blended in at small percentages to reduce cost. Still another example is a non-woven outer-cover made of stretchable or elastic materials, such as elastomeric composites of non-woven(s) and elastic membranes or a single layer of elastic material. The elastomeric composite can comprise an inner layer of pre-stretched extruded elastic film sandwiched between and attached to a pair of non-woven webs. The non-woven webs may consist of spun-bond web, thermal-bond web, or a combination of the two. Preferably, the elastic film is made of synthetic rubber and the non-woven made of spun-bond polypropylene.

Other materials for forming the back sheet 12 may include polypropylene films, co-extruded films (polyethylene and ethylene vinyl acetate), co-polymer films (polyethylene/polypropylene), and polylaminates (polypropylene nonwoven and polyethylene film). Still another example is a film made of a "breathable" microporous polyethylene. Suitable breathable films are available from Exxon Chemical Company, Buffalo Grove, Ill., USA. This material allows water vapor to pass through it over time, while being impervious to liquids. The water vapor transmission rate may range from 200-2000 grams per square meter per 24-hour period.

In order to enable waste to quickly and efficiently pass through the top sheet 14, the top sheet 14 is preferably liquid permeable (e.g., hydrophilic). In particular, the top sheet may be selected from a variety of textile-like films and fabrics. Suitable fabrics include non-woven materials that are pervious to liquid, soft and pliable. Preferred non-woven materials include spun-bonded polypropylene; spunbonded polyethylene; thermally bonded webs of staple fibers preferably polypropylene shape or sheath/core bi-component fibers having a core of polyester or polypropylene and a sheath of polyethylene. To enhance the fluid control properties of the aforementioned liners, surfactants or wetting agents typified by X-100 and Triton X-102 available from Rohm & Haas Company of Philadelphia, Pa., USA. may be applied to the fluid receiving zones of the liner selectively having the outer zones untreated to reduce migration of excreted fluid such as urine into the outer regions of the absorbent article leading to leakage. If desired, the top sheet 14 may be formed of a liquid impermeable material having plural apertures or pores extending therethrough so as to make the material liquid permeable.

The liquid transfer layer 27 is a hydrophilic liquid distributing transfer layer optionally provided to manage, transport, accommodate and/or direct urine or other body fluid received from the top sheet "target" or fluid "insult" zone (i.e., the area at which the body fluid(s) gain(s) ingress into the article) into the absorbent core 25.

The absorbent core 25 is centered in the absorbent article 10 and extends along a substantial portion of the length of the chassis 20. The core 25 can be made up of any suitable absorbent material, as well as combinations of different types of absorbent materials. For example, the absorbent core 25 may be formed of a mixture of pulp fluff and SAP. Examples of SAP include polyacrylamides, polyvinyl alcohol, polyacrylates, various grafted starches, and the like. A desired super absorbent material is a cross-linked polysodium acrylate, which can be purchased from Chemdal Corporation, Palatine, Ill., under the trademark ASAP 2260. The super absorbent materials can be in various geometric forms, such as various shaped particles, fibers, foams, and layers.

Moreover, the core 25 can be of any shape and can be a single, integral absorbent structure, or can comprise a plurality of individual separate absorbent structures and/or absorbent materials that are operably assembled together. It can also consist of air-laid non-woven web that contains superabsorbent particles and/or super-absorbent fibers, polymeric binder and cellulose pulp fibers. The absorbent core is centered along the transverse direction and registered in the machine, or longitudinal, direction within the article's chassis.

The chassis 20 also includes a pair of leg cuffs 22 to provide leakage control in the crotch region. The leg cuffs 22 are generally positioned in the crotch portion 5 of the chassis 20. Each leg cuff 22 extends longitudinally adjacent a respective longitudinal edge 15 of the absorbent core 25. In use, the cuffs 22 are drawn against the body between the inner thighs. Specifically, the elasticized belts 16 draw the legs cuffs against the inner thighs of the wearer to control leakage through the boundaries of the crotch portion 5 of the chassis 20. Additional benefits and features of leg cuff construction are disclosed in U.S. application Ser. No. 11/238,738. The disclosure of U.S. application Ser. No. 11/238,738 is incorporated herein by reference in its entirety.

In addition to the leg cuffs 22, although not shown, an elasticized region may be incorporated with the longitudinal edges 15 of the posterior portion 3 and anterior portion 7 of the chassis 20 for improved fit, adjustability, and leakage control. Also, the waist edges 21 of the chassis 20 may be elasticized, i.e., include elastic members, for improved adjustability, article fit and comfort in the waist area.

The exemplary elasticized belt 16 illustrated in FIGS. 1A-1C facilitates simultaneous adjustment of the crotch portion 5 and the waist segment of the chassis 20. Other exemplary embodiments of elasticized belts are envisioned whereby the end portions of the belt are separable into at least two belt segments, otherwise known as stretch ear segments, whereby a user may adjust the crotch portion independently of the waist segment. The plurality of belt segments are generally analogous to stretch ear segments. Three such exemplary embodiments are illustrated in FIGS. 2-4.

Figure 2:
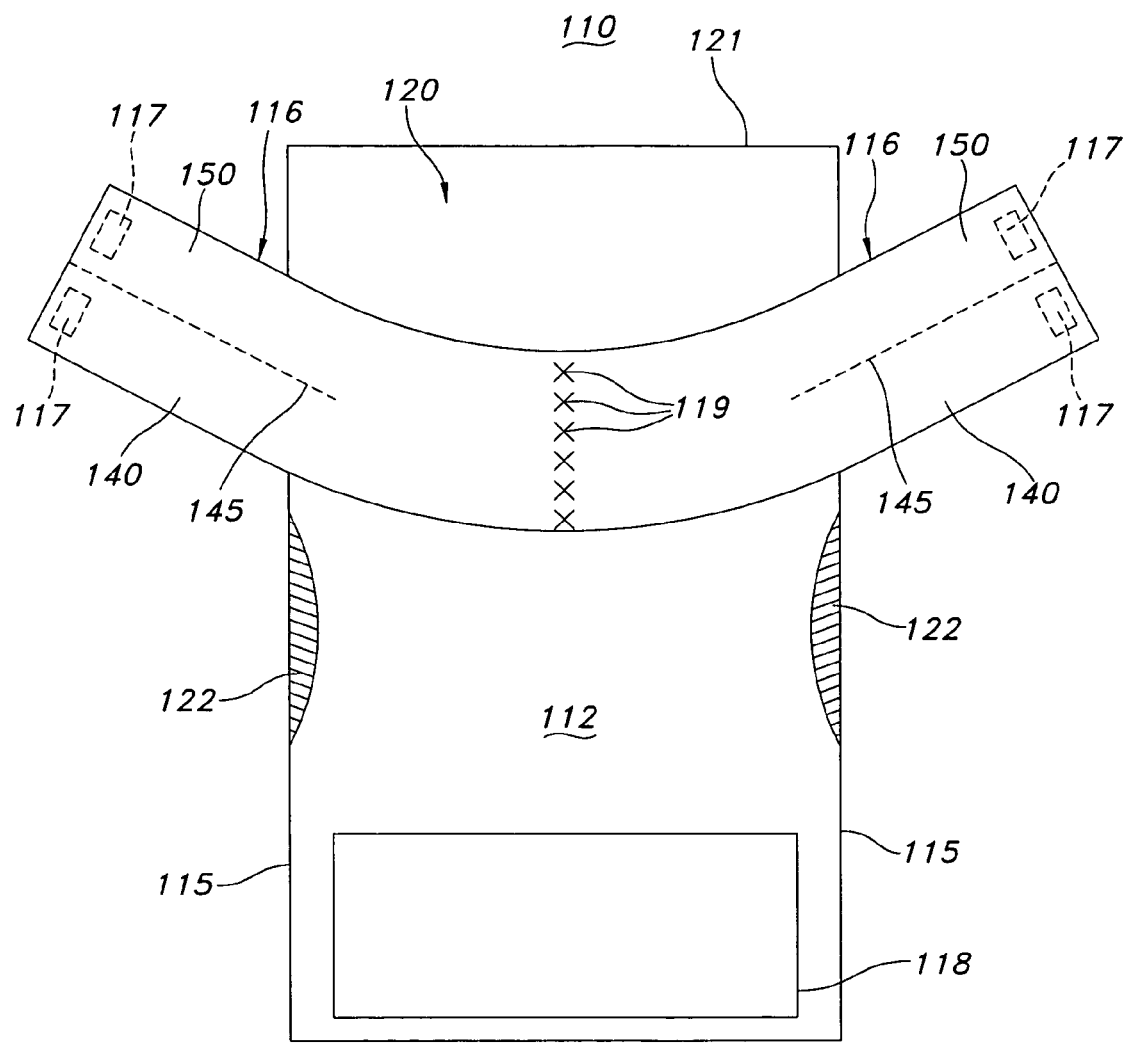
FIG. 2 is a plan view of the garment facing side of another exemplary absorbent article.
Figure 3A:
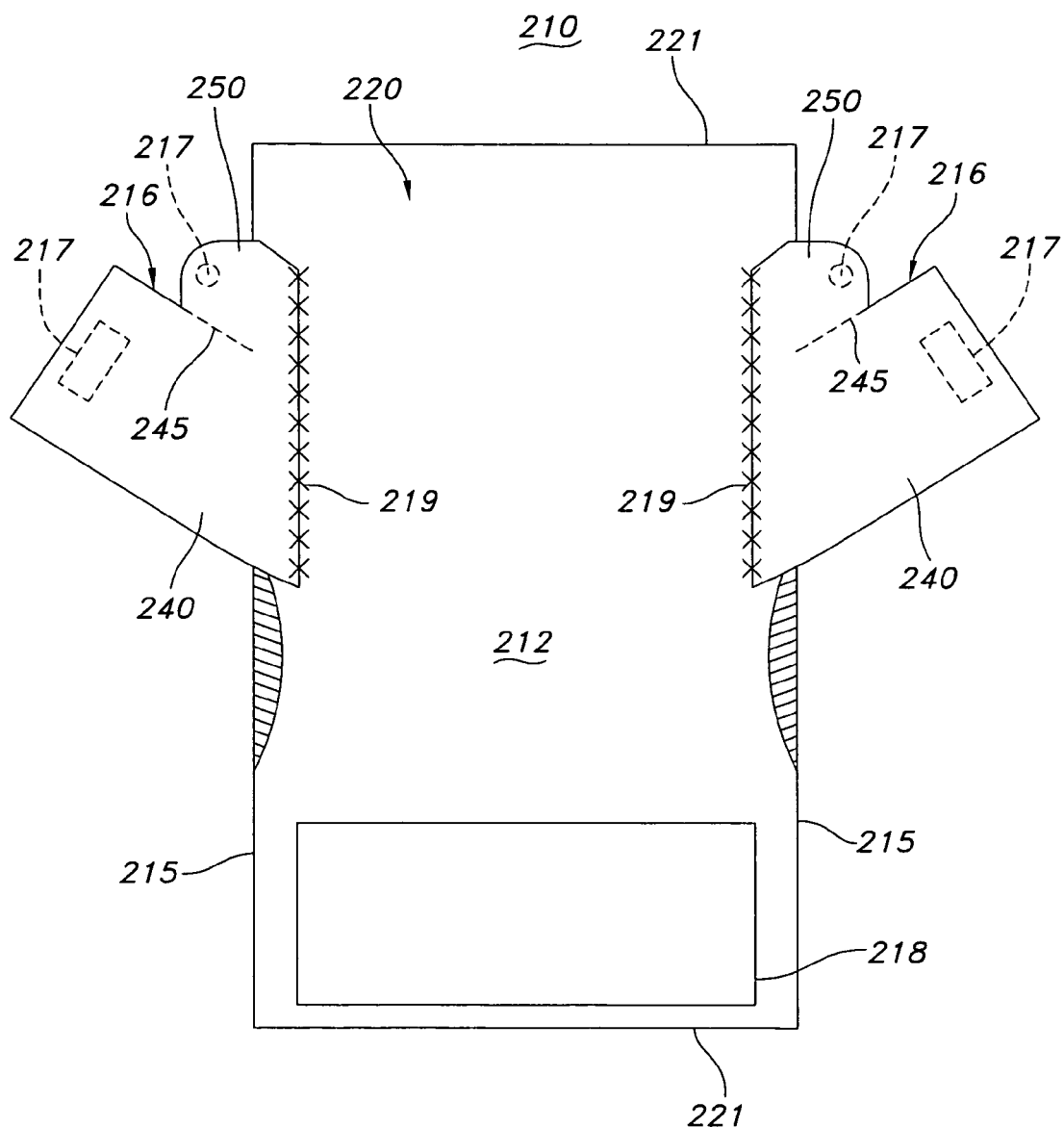
FIG. 3A is a plan view of the garment facing side of yet another exemplary embodiment of an absorbent article.
Figure 3B:
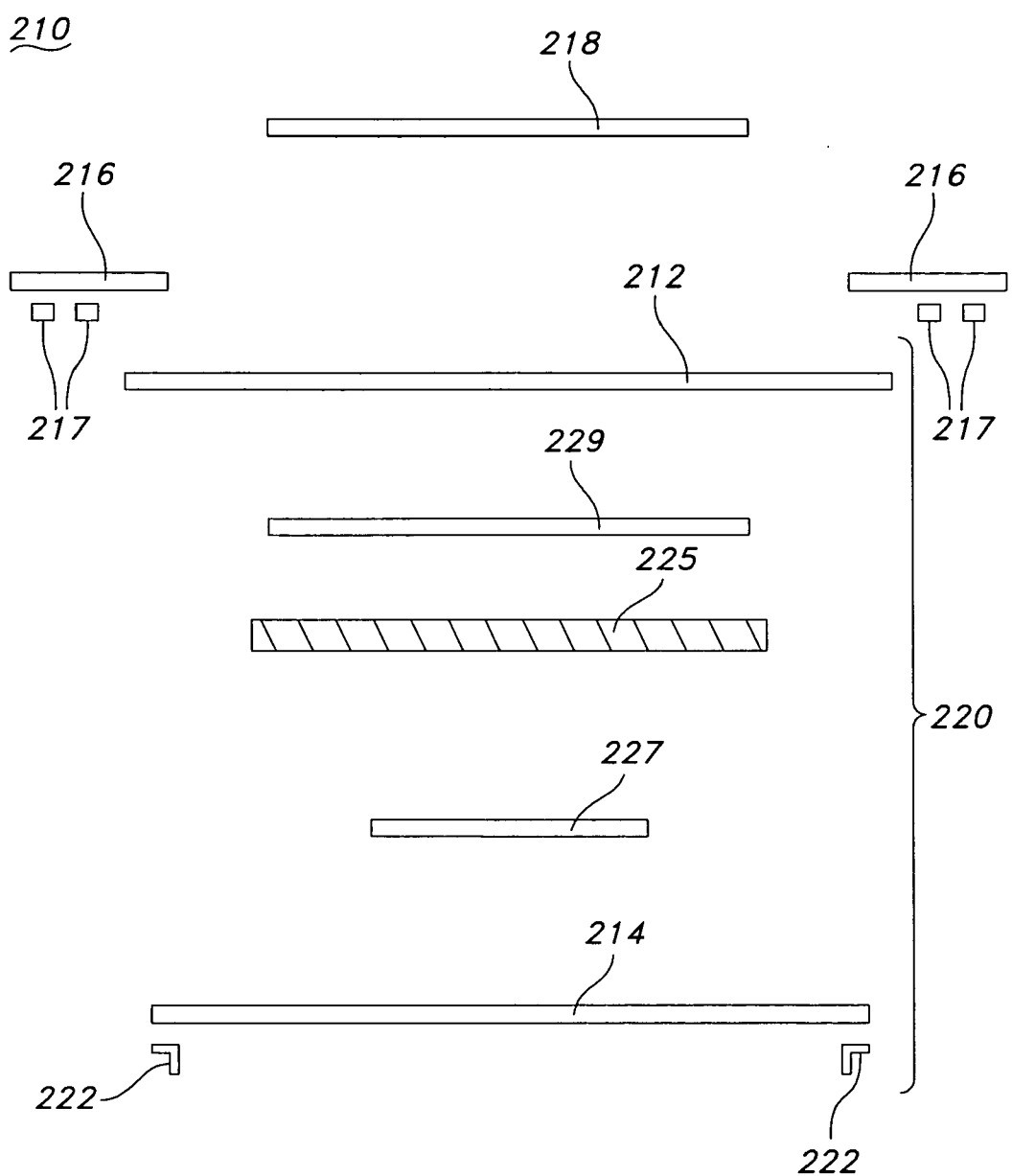
FIG. 3B is an exploded end view of the absorbent article of FIG. 3A.
Figure 4:
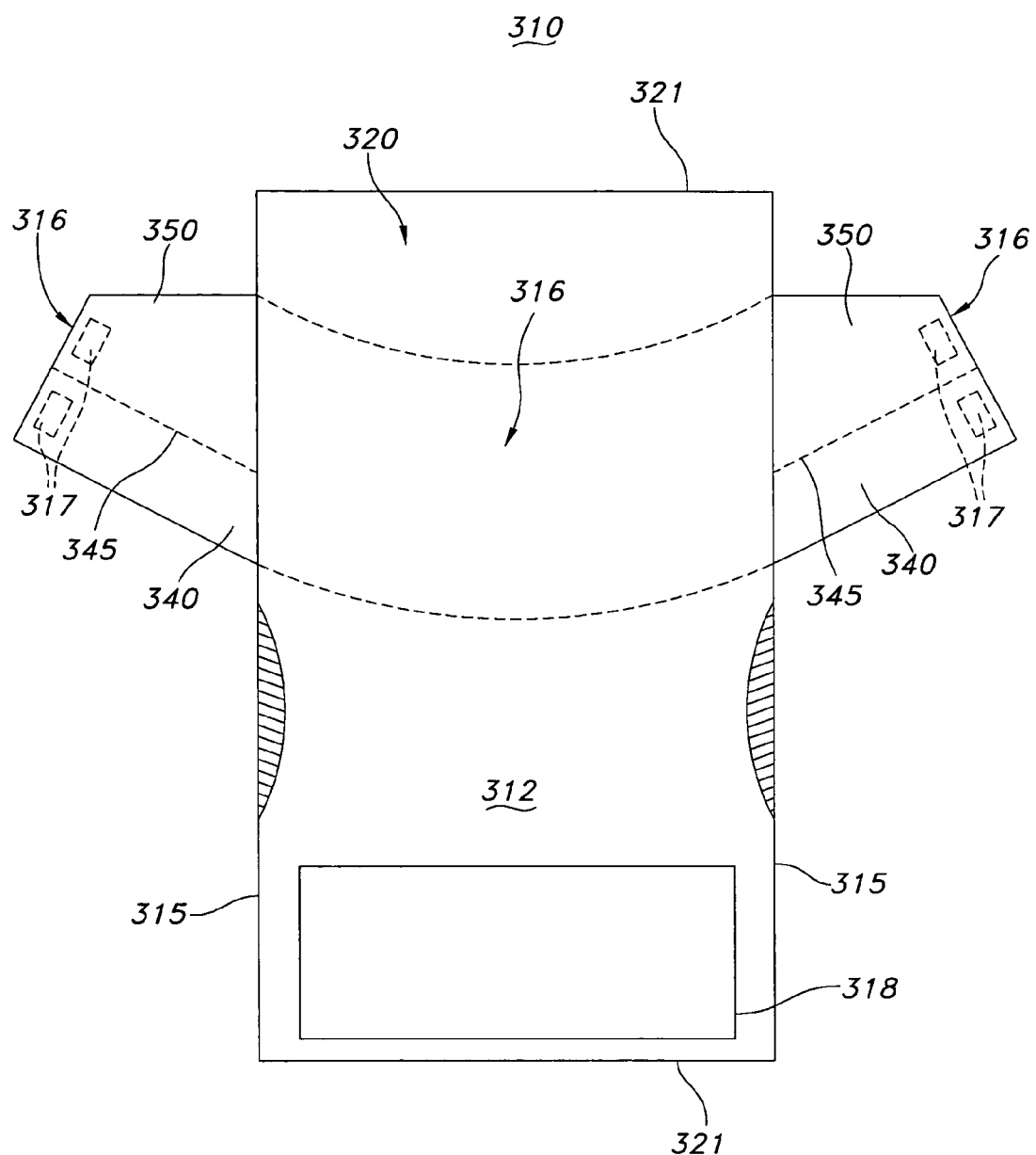
FIG. 4 is a plan view of the garment facing side of still another exemplary embodiment of an absorbent article.

In the exemplary embodiments illustrated in FIGS. 2-4, adjustment of the crotch portion 5 and the waist segment is independently controlled by a particular stretch ear segment. The stretch ear segments may be of different length, width, thickness, shape, material composition, and/or elasticity, for example, to serve any purpose or achieve any desired fit.

Referring now to FIG. 2, another exemplary embodiment of an absorbent article 110 is illustrated. The absorbent article 110 is similar to article 10, with the exception of the elasticized belt 116. Each end portion of the elasticized belt 116 comprises an upper stretch ear segment 150 and a lower stretch ear segment 140 that is contiguous with the upper stretch ear segment 150. The contiguous stretch ear segments 140 and 150 are at least partially separable along a perforated portion 145.

The length, width and shape of the stretch ear segments 140 and 150 are substantially similar, as shown in FIG. 2; however, the length, width and shape of the stretch ear segments may vary.

The ear segments 140 and 150 are adjusted independently to separately control fit of the crotch portion 5 and the waist size of the article 110. Because waist and leg sizes vary widely, the independent stretch ear segments 140 and 150 are particularly useful for individualized comfort. Generally, the upper ear segment 150 is positionable for controlling the waist fit of the article because the upper ear segment 150 is positioned closest to the waist edge 121 of the posterior portion 3. As stated above with reference to FIG. 1A, the waist edges 121 of the posterior and anterior portions 3, 7 of the chassis 120 form the waist segment of the article; thus, the stretch ear closest to the waist edge 121 controls the waist fit.

The lower ear segment 140 is positionable for controlling the crotch fit and/or leg fit of the article 110 because the lower ear segment 140 is mounted at or near the crotch portion 5 of the chassis 120. The lower ear segment 140 draws the crotch portion 5 of the chassis against the inner thigh of the wearer.

In use, the contiguous ear segments 140 and 150 are partially separable by tearing the perforated portion 145. Thereafter, the independent ear segments 140 and 150 may be releasably coupled to a variety of locations on the article 110 using fasteners 117 that are positioned on the end portions of the individual ear segments 140 and 150. In a first mounting configuration, the ear segments 140 and 150 may be coupled to separate locations of the fastener 118, or separate locations on the surface of the back sheet 112 (if fastener 117 is a position adhesive). Secondly, the ear segments 140 and 150 may be coupled to a surface of an opposing ear segment 140 and 150. Thirdly, one of the ear segments, e.g. ear segment 150, may be coupled to fastener 118, and the adjacent ear segment, i.e. ear segment 140, may be coupled to a surface of the ear segment 150 that is coupled to fastener 118, or vice versa. Additionally, the ear segments can cross over one another or can diverge from one another.

It should be understood that the ear segments 140 and 150 may be configured in a variety of different configurations and locations, in addition to those configurations listed above, to achieve any desired waist fit and/or crotch fit and/or leg fit. Of course, the contiguous ear segments 140 and 150 may not be separated and may instead be used together to simultaneously adjust the waist and crotch fit of the article, if so desired.

Although the stretch ear segments 140 and 150 may be coupled in any particular order, it may be convenient for a user of limited dexterity to initially secure the waist segment of the article 110 by coupling the ear segment 150 to the anterior portion 7. Thereafter, the ear segment 140 may be coupled to the anterior portion 7 (or other component of the article 110) to draw the crotch portion toward the body of the wearer. By securing the waist segment of the article first, the user may adjust the position of the crotch portion 5 without grasping the entire article.

Although not shown, the belt 116 may not necessarily include the perforated portions 145, as the stretch ear segments 140 and 150 may be discretely formed. Additionally, although the stretch ear segments 140 and 150 are formed from the same belt 116, in another embodiment, not illustrated herein, the ear segments 140 and 150 may be discrete components. To that end, in such an embodiment, the length, width, shape, material, and/or elasticity of the discrete ear segments may be unequal.

Referring now to FIGS. 3A and 3B, another exemplary embodiment of an absorbent article 210 is illustrated. The absorbent article 210 is similar to article 110, with the exception of the stretch ears 216. In lieu of the belts 16 and 116 shown in the previous exemplary embodiments, the absorbent article 210 includes two stretch ears 216 positioned on opposite sides of the article. The stretch ear segments extend beyond the longitudinal edges 215 along an acute angle, with respect to the waist edges 221. A fastener 217 is mounted to each ear segment. The fastener 217 is configured to be coupled to fastener 218, the back sheet 212, or any other surface of the article to achieve any desired fit.

Each stretch ear 216 includes an upper ear segment 250 and a contiguous lower ear segment 240, that are at least partially separable along a perforated portion 245. One end of each stretch ear 216 is fixed to the posterior portion 3 and the crotch portion 5 of the chassis at the attachment points 219 (eleven shown for purposes of illustration). More particularly, the upper ear segment 250 is fixed partially or completely to the posterior portion, and the lower ear segment 240 is fixed partially or completely to the crotch portion 5 of the chassis 220. However, it should be understood that the location of the attachment points may vary.

Generally, the upper ear segment 250 is positionable for controlling the waist fit of the article because the upper ear segment 250 is positioned closest to the waist edge 221 of the posterior portion 3. As stated above, the waist edges 221 of the posterior and anterior portions 3, 7 of the chassis 220 form the waist segment of the article; thus, the upper ear segment 250, which is positioned closest to the waist edge 221, controls the waist fit of the article. In practice, the upper ear segment 250 is positioned to extend between the anterior and posterior portions of the chassis 220. The upper ear segment 250 may be fixed to the posterior portion 3 of the chassis and releasably coupled to the anterior portion 7 of the chassis, as shown, or, alternatively the upper ear segment 250 may be fixed to the anterior portion 7 of the chassis and releasably coupled to the posterior portion 3 of the chassis to achieve the same result.

The lower ear segment 240 is intended to draw the crotch portion 5 of the chassis against the inner thigh and/or leg of the wearer. The lower ear segment 240 is positionable for controlling the crotch-area fit of the article 210 because the lower ear segment 240 extends between the crotch portion 5 and the anterior portion 3. The lower ear segment 240 may be fixed to the crotch portion 5 of the chassis and releasably coupled to the anterior portion 7 of the chassis, as shown, or, alternatively the lower ear segment 240 may be fixed to the anterior portion 7 of the chassis and releasably coupled to the crotch portion 5 of the chassis to achieve the same result.

In practice, the stretch ears segments 240 and 250 may be separated along the perforated portion 245, and separately applied to any surface of the absorbent article for independent control of the waist and crotch fit of the absorbent article. Alternatively, the stretch ear segments 240 and 250 may remain united, as shown, (i.e., not separated along perforated portion 245) and together applied to any surface of the absorbent article to simultaneously adjust the waist and crotch fit of the absorbent article.

According to this exemplary embodiment, the lower ear segment 240 is neither the same size nor shape as the upper ear segment 250. Furthermore, the stretch ear segments may be of different length, width, thickness, shape, material composition, and/or elasticity, for example, to serve any purpose or achieve any desired fit. Moreover, the fasteners 217 may be of different size or shape, as shown.

An exploded view of the absorbent article 210 is illustrated in FIG. 3B. The construction of the absorbent article 210 is similar to the construction of the absorbent article 10 shown in FIG. 1C, with the exception that the belt 16 is replaced by two stretch ears 216 positioned on opposing sides of the backsheet 212. The stretch ears 216 may be coupled to the back sheet 212, as shown, or, alternatively, the stretch ears 216 may be interposed between the back sheet 212 and the top sheet 214.

Referring now to FIG. 4, another exemplary embodiment of an absorbent article 310 is illustrated. The absorbent article 310 is similar to article 110, with the exception of the shape of the stretch ear segments 340 and 350, and the location of the belt 316. Similar to belt 116, the belt 316 is formed from a single component. Each end portion of the belt 316 includes an upper ear segment 350 and a contiguous lower ear segment 340. The contiguous ear segments 340 and 350 are at least partially separable along a perforated portion 345.

However, unlike belts 16 and 116 or stretch ears 216, in this exemplary embodiment the belt 316 is partially positioned within the interior of chassis 320, between the back sheet 312 and the top sheet (not shown). The segment of the belt 316 positioned with the chassis 320 is illustrated in broken lines (with the exception of perforated portion 345). With reference to FIG. 1C, the belt 316 may be positioned within the interior of the chassis 320 between the film layer 29 and the absorbent core 25, or, alternatively, the belt 316 may be positioned between the back sheet 12 and the film layer 29. The belt 316 may be permanently mounted to the film layer 29, the absorbent core 25, the back sheet 312 and/or the top sheet at one or more locations (not shown).

In assembly, the longitudinal edges 315 of the top sheet and the back sheet 312 may be sealed together, with the exception of where the belt 316 intersects the longitudinal edges 315 of the chassis 320. In those regions, the top sheet and the back sheet 312 may optionally be sealed to the surfaces of the belt 316.

Although the invention is illustrated and described herein with reference to specific embodiments, the invention is not intended to be limited to the details shown. Rather, various modifications may be made in the details within the scope and range of equivalents of the claims and without departing from the invention. For example, the material of the belts and stretch ears may be elastic, inelastic or formed from a fastening material such as VELCRO. The fasteners 17, 117, 217, 317 and 18, 118, 218, 318 may be composed of any fastening material known in the art, such as VELCRO, position adhesive, adhesive, co-adhesive, and the like. Furthermore, although the belt(s) are shown and described as permanently mounted to the posterior and crotch portions and configured for releasable mounting to the anterior portion of the chassis, the belt(s) may instead be permanently mounted to the anterior and crotch portions and releasably coupled to the posterior portion of the chassis.

Also, the embodiments selected for illustration in the figures are not shown to scale and are not limited to the proportions shown.

What is claimed is:

1. An absorbent article comprising:
   a chassis having a posterior portion positionable against a posterior of a wearer, a waist edge extending between side edges, an anterior portion and a crotch portion; and
   a belt coupled to the chassis, said belt having a top edge and a central portion extending between the side edges of said chassis and end portions extending outwardly beyond the side edges of the chassis, the belt comprising an unfastened configuration in which the end portions remain unattached to the anterior portion of the chassis and a fastened configuration in which the end portions are directly attached to the anterior portion of the chassis;
   wherein, when the belt is in the unfastened configuration, a distance between the top edge at the central portion of the belt and the waist edge of the posterior portion of the chassis is greater than a distance between the top edge at the end portions of the belt and the waist edge of the posterior portion of the chassis.

2. The absorbent article of claim 1 said belt being positioned to draw the chassis about a leg of a wearer.

3. The absorbent article of claim 1 wherein said belt is formed from an elastic material.

4. The absorbent article of claim 1 further comprising a fastener portion disposed on at least one of said end portions of said belt.

5. The absorbent article of claim 4 wherein said fastener portion is configured to be releasably coupled to said chassis at a location closer to the waist edge of said chassis than the location of said central portion of said belt.

6. The absorbent article of claim 1 wherein said belt includes a curved or slanted portion.

7. The absorbent article of claim 1 wherein said end portions are configured to be fastened between said crotch portion and said anterior portion.

8. The absorbent article of claim 7 wherein said belt is fixed to the crotch portion of said chassis and releasably coupled to said anterior portion of said chassis.

9. The absorbent article of claim 7 wherein said belt is fixed to the anterior portion of said chassis and releasably coupled to said crotch portion of said chassis.

10. A method of forming an absorbent article comprising the steps of:

coupling a central portion of a belt to a posterior portion of a chassis such that end portions of the belt extend beyond side edges of the chassis, the belt having a top edge, the chassis further comprising an anterior portion, the belt comprising an unfastened configuration in which the end portions remain unattached to the anterior portion of the chassis and a fastened configuration in which the end portions are directly attached to the anterior portion of the chassis; and orienting the belt such that, when the belt is in the unfastened configuration, a distance between the top edge at the central portion of the belt and a waist edge of the posterior portion of the chassis is greater than a distance between the top edge at the end portions of the belt and the waist edge of the posterior portion of the chassis.

11. The method of claim 10 further comprising coupling fasteners to the end portions of the belt.

12. The method of claim 11 further comprising configuring the fasteners for releasable engagement of the anterior portion of the chassis.

\* \* \* \* \*